(12) United States Patent
Gilbert et al.

(10) Patent No.: US 6,314,316 B1
(45) Date of Patent: Nov. 6, 2001

(54) NONPENETRATING ELECTROPORATION DEVICE AND METHOD

(75) Inventors: Richard Gilbert; Mark Jaroszeski, both of Tampa; Richard Heller, Temple Terrace, all of FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/213,218

(22) Filed: Dec. 17, 1998

(51) Int. Cl.⁷ ..................................................... A61N 1/30
(52) U.S. Cl. ............................................. 604/20; 604/500
(58) Field of Search ................................ 604/19, 20, 500, 604/501; 435/173.6, 461

(56) References Cited

U.S. PATENT DOCUMENTS

| | | | |
|---|---|---|---|
| 1,099,062 | * 6/1914 | Laposkey | 607/139 |
| 4,970,154 | * 11/1990 | Chang | 435/172.2 |
| 5,318,514 | 6/1994 | Hofmann . | |
| 5,439,440 | 8/1995 | Hofmann . | |
| 5,674,267 | 10/1997 | Mir et al. . | |
| 5,707,349 | * 1/1998 | Edwards | 604/22 |
| 5,869,326 | * 2/1999 | Hofmann | 435/285.2 |
| 5,873,849 | * 2/1999 | Bernard | 604/20 |
| 5,983,130 | * 11/1999 | Phipps et al. | 604/20 |
| 6,009,345 | * 12/1999 | Hofmann | 604/20 |

FOREIGN PATENT DOCUMENTS

WO 96/39226  12/1996  (WO) .
WO 98/47562  10/1998  (WO) .

* cited by examiner

Primary Examiner—Sharon Kennedy
Assistant Examiner—Michael Hayes
(74) Attorney, Agent, or Firm—Allen, Dyer, Doppelt, Milbrath & Gilchrist, P.A.

(57) ABSTRACT

The manipulator includes a support and at least one member affixed to and extending away from the support. The member has at least two differentially activatable electrodes. The electrodes are configured to establish a first electromagnetic field in vivo between selected electrodes sufficient to manipulate a molecule relative to a target tissue and to establish a second, typically higher, electromagnetic field sufficient to cause transient permeability of a cell membrane within the target tissue. One method of using the device is for enhancing the delivery of a molecule into a tissue site. In a related embodiment the device may be used to cause the electromigration of at least two components of a multicomponent reactive system into apposition to permit a reaction to occur at a desired target tissue site. The target tissue may comprise a tumor, organ, or wound site.

15 Claims, 4 Drawing Sheets

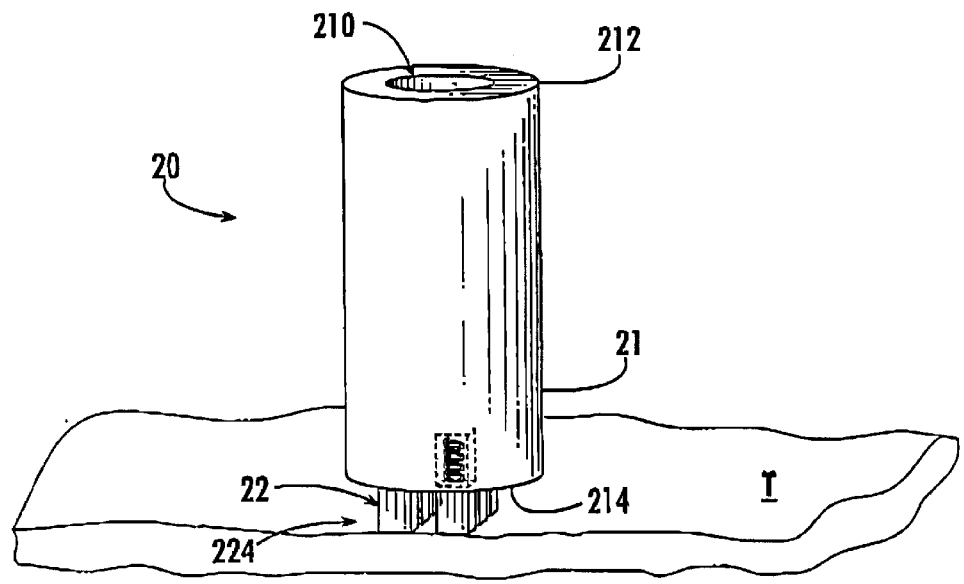
FIG. 5.
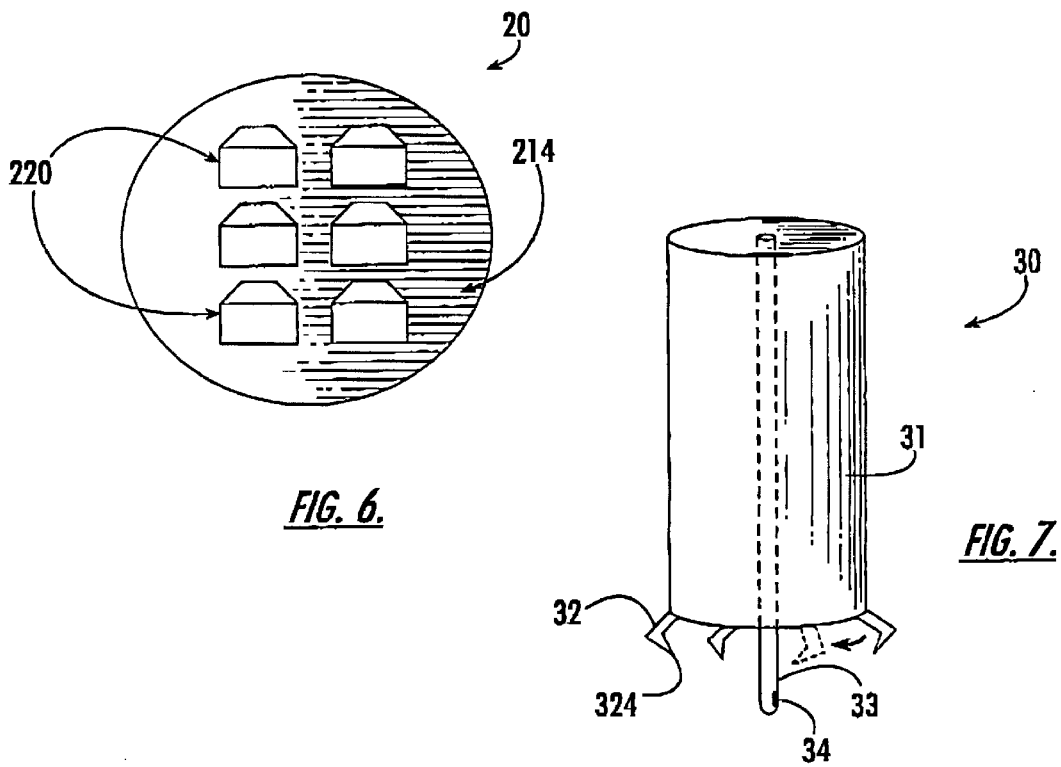
FIG. 6.
FIG. 7.

NONPENETRATING ELECTROPORATION DEVICE AND METHOD

BACKGROUND OF THE INVENTION

1. Field of the Invention

The present invention relates to methods and apparatus for delivering molecules into a target cell, and, more particularly, to such methods and apparatus for achieving such delivery through electroporation.

2. Description of Related Art

The effect of electromagnetic fields on cell membranes has been studied since the 1960s. Early research focused on describing observations that an applied electric field can reversibly break down cell membranes in vitro. Throughout the 1970s the topic was more common in the literature and continued to focus on describing the phenomenon that resulted from brief exposure to intense electric fields as well as the entry of exogenous molecules to the cell interior as a result of membrane breakdown. Applications began to emerge along with a better understanding of reversible membrane breakdown in the 1980s.

Prior research led to the current understanding that exposure of cells to intense electric fields for brief periods of time temporarily destabilized membranes. This effect has been described as a dielectric breakdown due to an induced transmembrane potential, and was termed "electroporation," or "electropermeabilization," because it was observed that molecules that do not normally pass through the membrane gain intracellular access after the cells were treated with electric fields. The porated state was noted to be temporary. Typically, cells remain in a destabilized state on the order of minutes after electrical treatment ceases.

The physical nature of electroporation makes it universally applicable. A variety of procedures utilize this type of treatment, which gives temporary access to the cytosol. These include production on monoclonal antibodies, cell-cell fusion, cell-tissue fusion, insertion of membrane proteins, and genetic transformation. In addition, dyes and fluorescent molecules have been used to investigate the phenomenon of electroporation. A notable example of loading molecules into cells in vivo is electrochemotherapy. The procedure utilizes a drug combined with electric pulses as a means for loading tumor cells with an anticancer drug, and has been performed in a number of animal models and in clinical trials by the present inventors. Also, plasmid DNA has been loaded into rat liver cells in vivo (Heller et al., FEBS Lett. 389, 225–28).

Protocols for the use of electroporation to load cells in vitro typically use a suspension of single cells or cells that are attached in a planar manner to a growth surface. In vivo electroporation is more complex because tissues are involved. Tissues are composed of individual cells that collectively make up a three-dimensional structure. In either case, the effects on the cell are the same. FIG. 1 illustrates details of the electroporation procedure. Electrodes and electrode arrays for delivering electrical waveforms for therapeutic benefit, including inducing electroporation, have been described by Bernard (WO 98/47562).

The loading of molecules by electroporation in vitro as well as in vivo is typically carried out by first exposing the cells or tissue of interest to a drug (FIG. 2). The cells or tissue are then exposed to electric fields by administering one or more direct current pulses. Electrical treatment is conducted in a manner that results in a temporary membrane destabilization with minimal cytotoxicity. The intensity of electrical treatment is described by the magnitude of the applied electric field. This field is defined as the voltage applied to the electrodes divided by the distance between the electrodes. Electric field strengths ranging from 1000 to 5000 V/cm have been used and are specific to the cells or tissue under investigation. Pulses are usually rectangular in shape; however, exponentially decaying pulses have also been used. The duration of each pulse is called pulse width. Molecule loading has been performed with pulse widths ranging from microseconds ($\mu s$) to milliseconds (ms). The number of pulses delivered has ranged from one to eight. Typically, multiple pulses are utilized during electrical treatment.

For molecules to be delivered to the cell interior by electroporation, it is important that the molecule of interest be near the exterior of the cell membrane at the time of electroporation. It is also important to have molecules near substantially all cells within a treated tissue volume in order to provide efficient delivery to substantially all cells within the treatment volume.

Currently, molecules are injected systemically or directly into the treatment site. No attempt is made to produce a specific distribution. These methods do not ensure that the distribution of molecules is sufficient to provide effective delivery to substantially all the cells.

Electropermeabilization of tumor cell membranes has been reported (Rols et al., *Nature Biotechnology* 16, 173, 1998) using applied electric pulses from surface electrodes in contact with the skin. Proteins and genes can be transferred into the cells by incorporating either the protein or a plasmid carrying a reporter gene. The efficiencies of transfer for the protein and plasmid were, respectively, 20 and 4%.

A first type of electrode known in the art comprises parallel-plate electrodes placed on opposite sides of the tumor. Other electrodes known in the art at the present time comprise needles that are inserted into or around the tissue of interest. A third type comprises a planar arrangement of parallel wires that can be placed on the surface of the tissue.

Electrodes and methods known in the art do not provide molecule movement during the preelectroporation time for electromigration, distribution, and postelectroporation time period when the cells are in a state of increased membrane permeability. The movement of molecules within the tissue is believed to effect an increase in the delivered quantity of molecules by enhancing movement into the cells.

SUMMARY OF THE INVENTION

It is therefore an object of the present invention to provide a device and method for manipulating molecules within a target tissue site.

It is an additional object to provide such a device and method for manipulating molecules while a target cell is in a permeabilized state.

It is a further object to provide such a device and method that can provide a desired electromagnetic field distribution within a target tissue.

It is another object to provide such a device and method that can be configured to activate a multicomponent labile system at a desired site.

It is yet an additional object to provide a system for effecting tumor regression.

It is yet a further object to provide a system for effecting in vivo gene delivery via electroporation and electromigration.

These objects and others are attained by the present invention, a device for manipulating a molecule in vivo relative to a target tissue. The device comprises a support and at least one member affixed to and extending away from the support. The member has at least two discrete electrodes, each electrode in circuit communication with a respective portion of a source of electrical energy and therefore being differentially activatable.

The discrete electrodes are configured to establish a first electromagnetic field in vivo between selected electrodes sufficient to manipulate a molecule relative to a target tissue. The electrodes are further configured to establish a second, typically higher, electromagnetic field sufficient to cause transient permeability of a cell membrane within the target tissue.

The device can be used, for example, with alternating current, direct current, pulsed alternating current, pulsed direct current, high- and low-voltage alternating current with variable frequency and amplitude, variable direct current waveforms, variable alternating current signals biased with variable direct current waveforms, and variable alternating current signals biased with constant direct current.

Several embodiments of the methods of the present invention include the use of a device as described above to enhance the delivery of a molecule such as a bioactive molecule, nucleic acid, amino acid, polypeptide, protein, antibody, glycoprotein, enzyme, oligonucleotide, plasmid DNA, chromosome, or drug, although this list is not intended to be exhaustive or limiting. In a related embodiment the device may be used to cause the electromigration of at least two components of a multicomponent reactive system into apposition to permit a reaction to occur at a desired target tissue site. The target tissue may comprise a tumor, an organ, or a wound site.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 2 (prior art) The process of delivering molecules by electroporation.

FIG. 5 A second embodiment of a nonpenetrating molecule manipulator, including multiple electrodes disposed on downwardly depending posts from a generally cylindrical support.

FIG. 6 A bottom plan view of the embodiment of FIG. 5.

FIG. 7 A side view of a third embodiment of a nonpenetrating molecule manipulator, including inwardly moving electrode-support members.

DETAILED DESCRIPTION OF THE PREFERRED EMBODIMENTS

Figure 1:
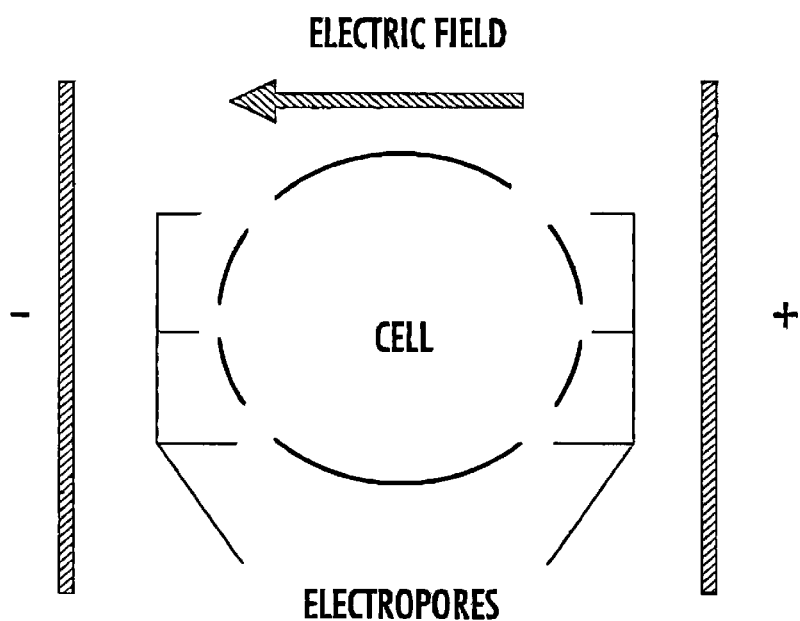
FIG. 1 (prior art) Two-dimensional depiction of electroporation of a cell subjected to an electromagnetic field. Regions of membrane breakdown, depicted as pores, are formed at the ends of cells facing the electrodes. Electromagnetic field exposure is achieved by applying a potential between electrodes − and +.
Figure 2A:
FIG. 2A. A tumor cell in vitro or in vivo is exposed to the molecule of interest.
Figure 2A:
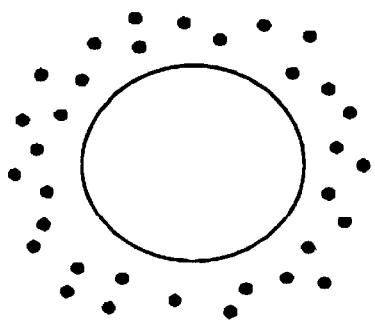
Figure 2B:
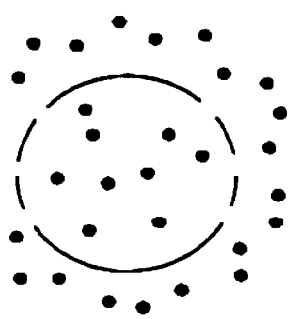
FIG. 2B. Direct current pulses are administered to the cells to cause a temporary membrane destabilization that allows the molecules to more freely enter the cell interior.
Figure 2C:
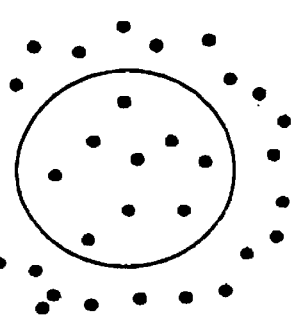
FIG. 2C. Cells return to their normal state after pulsation, leaving the drug within the cells.

A description of the preferred embodiments of the present invention will now be presented with reference to FIGS. 3–9.

A first embodiment of a nonpenetrating device 10 for manipulating a molecule M in vivo relative to a target tissue T (FIGS. 3 and 4) comprises a support that comprises a generally cylindrical post 11 having a portal 110 therethrough from a top end 112 to a bottom end 114.

Figure 3:
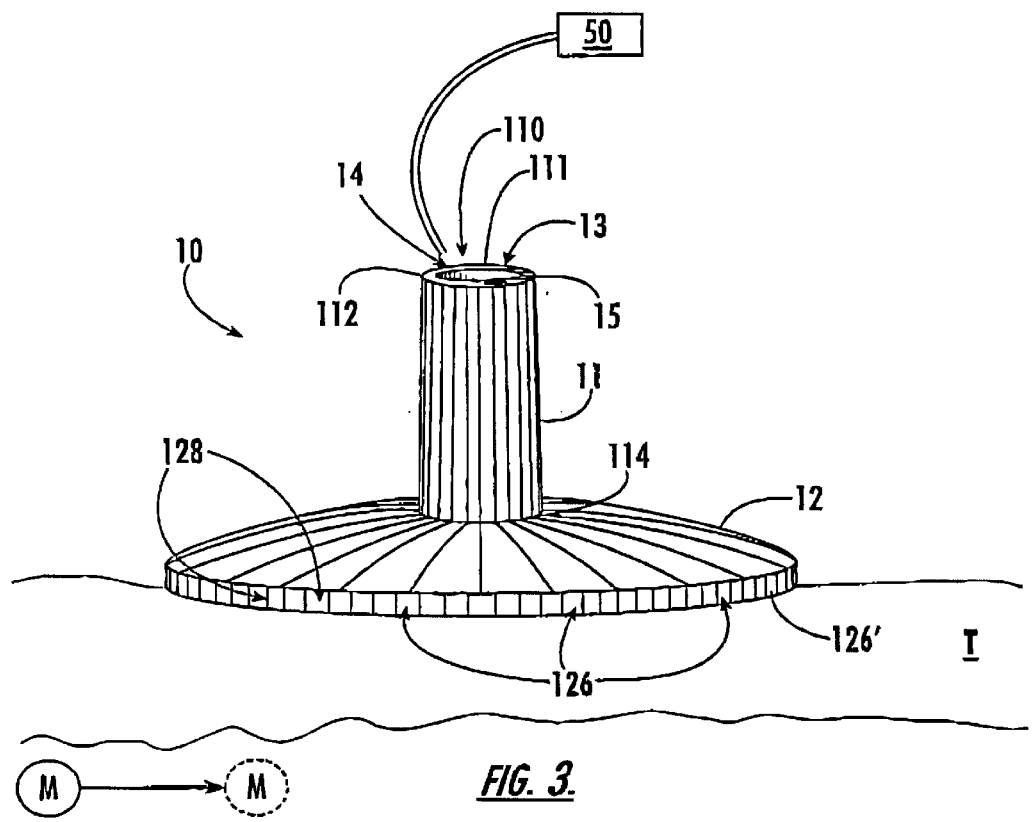
FIG. 3 A first embodiment of a nonpenetrating molecule manipulator, including an annular member having electrodes spaced apart by nonconductive material.
Figure 4:
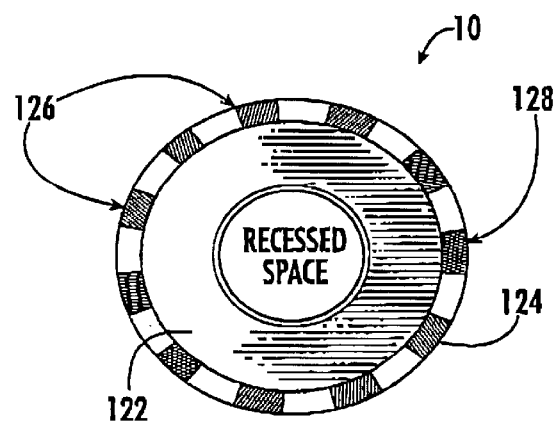
FIG. 4 A bottom plan view of the embodiment of FIG. 3.
Figure 8:
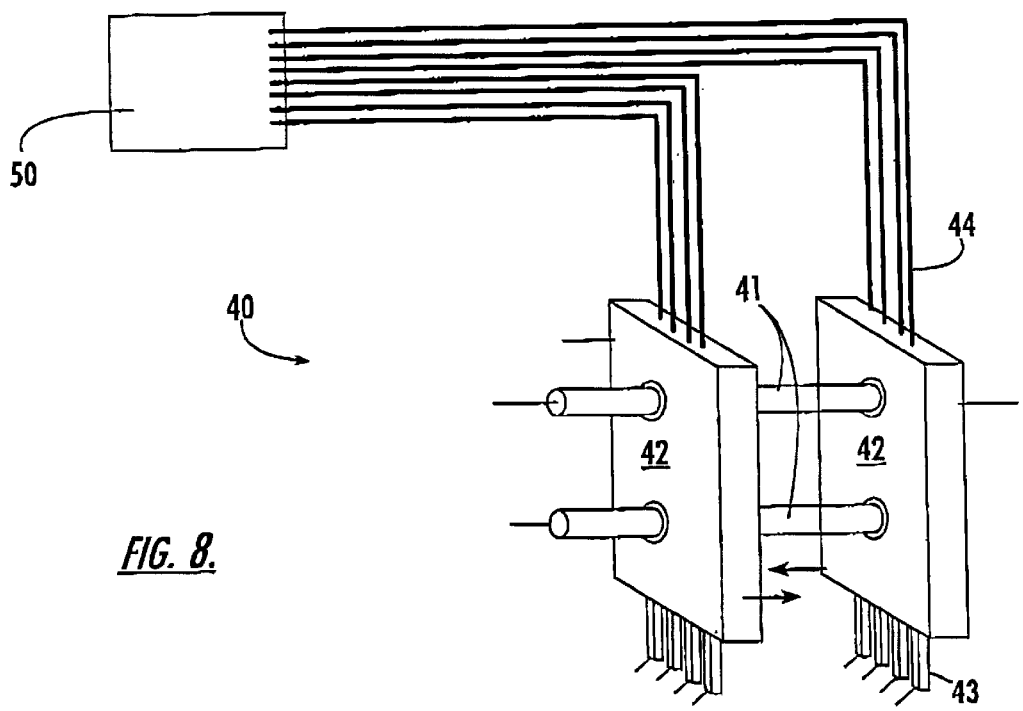
FIG. 8 A side perspective view of a fourth embodiment of a nonpenetrating molecule manipulator, including a pair of electrode-bearing members having an adjustable separation therebetween.
Figure 9:
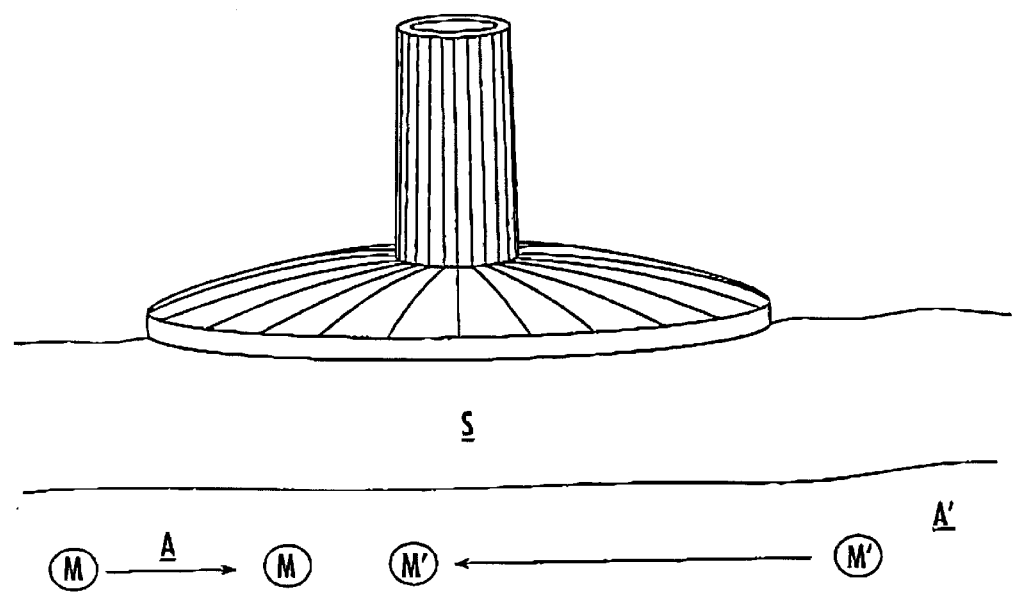
FIG. 9 The use of a nonpenetrating molecule manipulator to bring components of a multicomponent reactive system into apposition at a target tissue site.

A generally disclike object 12 is affixed to the post's bottom end 114. The disc 12 has a bottom surface 122 with an outer downwardly depending annulus 124 that comprises alternating radial sectors of conductive 126 and nonconductive 128 areas. The conductive sectors 126 serve as the electrodes, and the nonconductive areas 128 serve to space the electrodes apart from each other. The annulus 124 is configured to surround a surface projection of a periphery of at least a portion of the target tissue T. In FIG. 3 the target tissue is T represented as the skin or surface of an organ, although this is not intended to be a limitation.

Preferably the disc 12 comprises a flexible material to permit shape adaptation with the selected portion of the target tissue. Also preferably the disc 12 has a transparent portion to permit visualization of the target tissue's selected portion therethrough.

An independent conductive lead 13 is in circuit communication with each of the conductive areas 128. Each lead 13 extends from the disc 12 through the post's portal 110 to the top end 112 thereof.

A plurality of contact means are positioned adjacent the post portal's top end 112 and in circuit communication with each lead 13. In a particular embodiment each contact means comprises a contact brush 14 that is affixed within the portal 110 against an inner wall 111 thereof. Interface means are positioned adjacent the post portal's top end 112 and has means for communicating with each contact brush 14 for establishing circuit communication with a signal generator 50. In a particular embodiment the interface means comprises a key interlock 15 that is insertable within the portal 110 at the top end 112. The key interlock 15 has a contact pad positioned for communication with each contact brush 14 in a manner well known in the art.

Each electrode 126 is in circuit communication with a respective portion of the source 50 of electrical energy. In a preferred embodiment this source comprises a pulse generator such as is known in the art (e.g., a PA-2000 or PA-4000, both from Cyto Pulse Sciences, Inc., Columbia, Md.; a T820, BTX, Inc., San Diego, Calif.) and adapted to deliver pulses of a predetermined shape, voltage, duration, and separation. In particular, the source 50 should be adapted to deliver voltage to each electrode 126 for establishing a first, low-level and a second, typically higher-level electromagnetic field in vivo between selected electrodes. Selective control of the application of electrical signals between the individual electrodes can be accomplished in different ways, e.g., via the PA-201 Programmable Pulse Switch in combination with the PA-4000 generator (both from Cyto Pulse Sciences, Inc., Columbia, Md.) or it can be done manually, mechanically, or electrically.

The low-level field is for manipulating the molecule M relative to the target tissue T, here shown as a mass. The higher-level field is for causing transient permeability of a cell membrane within the target tissue T. Such a permeability is useful for permitting the molecule M to enter the interior of the cell (see FIGS. 1 and 2).

In use, the electrodes 126 are typically activated in opposing pairs, so that at least one electrode of each of a pair of electrodes 126 can be adapted to provide at least one pair of opposite-polarity voltages approximately simultaneously. Of course, other combinations can easily be envisioned by those of skill in the art. Further, it may be desired to selectively apply voltage to each electrode pair in a predetermined pattern. Such a means for imposing a preselected pattern may include, for example, a software program for driving a pulse generator to deliver signals to each selected electrode in the preselected pattern.

A second embodiment of a nonpenetrating device 20 for manipulating a molecule M in vivo relative to a target tissue T (FIGS. 5 and 6) comprises a generally cylindrical support 21 having a lumen 210 extending from a top end 212 through to a bottom end 214. A plurality of downwardly depending posts 22 are affixed adjacent the support's bottom end 214, with each post 22 having a conductive area 220 on a bottom surface 224 thereof. The posts 22 are disposed in spaced-apart relation from each other, and the conductive areas 220 comprise the electrodes.

In a particular embodiment, each post 22 is movably affixed to the support 21. Each post 22 is axially movable between a first position and a second position lower than the first position and is biased to the second position. This movement is for achieving contact between each post 22 and a target tissue T surface. In a specific type of movable post 22, as shown in FIG. 5, each post 22 is affixed to the support 21 in spring-loaded fashion. Such movement permits a generally planar support bottom surface 214 to permit electrode contact with a nonplanar surface.

The lumen 210 may be used, for example, as a syringe guide to permit the introduction of the desired molecule into the tissue T prior to activating the electrodes.

In FIG. 7 is shown a third embodiment 30 of a device similar to that 20 above. In this embodiment the posts 32 have pointed conductive bottom tips 324 that are disposed at a radially inwardly facing angle to each other. Each post 32 is inwardly movable between a first position and a second position wherein the tips 324 are closer together than in the first position. The second position is for gripping tissue T between the tips 324.

Another feature illustrated in this embodiment comprises a hollow needle 33 extending through the support 31. The needle 33, the tip of which extends beneath the posts 32, can carry a dose of the substance to be introduced into the tissue T or can be used as a portal through which the introduction can take place. In a related embodiment the needle 33 is movable axially to permit a selection of the depth of penetration.

A fourth embodiment 40 of the device (FIG. 8) includes a support 41 that movably holds a pair of insulating plates 42 in generally parallel fashion. In the embodiment shown the plates 42 comprise generally rectangular planar members. The support 41 includes means for altering the separation between the plates 42, which is useful for gripping tissue T therebetween.

Each plate 42 has a plurality of electrodes 43 affixed to its inward-facing surface 424, and leads 44 are connected to each electrode 43 for providing circuit communication with a signal generator 50.

Several embodiments of methods of the present invention will now be disclosed. These methods will be illustrated with the device 10 described above, although this is not intended as a limitation, since any of the devices 10, 20, 30, or 40 could be used therein, or other equivalents appreciated by one of skill in the art.

A first embodiment comprises a method for achieving an improved distribution and delivery of a desired molecule M into a target tissue T. This method comprises the steps of placing at least two electrodes 126 generally adjacent but in nonpenetrating fashion to a surface of a target tissue T. A substance that includes the desired molecule M, such as a solution thereof, is introduced into the body systemically into an area near or on the target tissue T, either before or after the positioning of the device 10.

A first electrical potential is established between a pair of electrodes 126–126' that is sufficient to cause electromigration of the desired molecule M from an initial location to a more desirable location on the target tissue T. In a particular embodiment the pulse height range is 1–15 V/cm in the millisecond range.

A second electrical potential is established between a pair of electrodes, which may or may not be the same electrode pair 126–126' as previously activated. The second potential is higher than the first electrical potential and is sufficient to cause electroporation in the target tissue T to enhancing a movement of the desired molecule M into a cell. Exemplary pulse height and duration ranges include, but are not intended to be limited to, 1–10,000 volts/cm and the nanosecond range. In a particular embodiment the pulse height range is 750–1500 V/cm over the millisecond range. Either or both of the potentials can be delivered in a series of predetermined sequence of pulses, each of which can comprise pulses delivered sequentially or simultaneously.

A second method is for delivering a bioactive molecule to a subcutaneous target tissue T. This method comprises the steps of, as above, introducing a substance containing the charged bioactive molecule M to a subcutaneous area adjacent the target tissue T. A device such as device 10 is placed generally adjacent but in nonpenetrating fashion to a target tissue T, and electrode pairs are again activated at a low and high level to achieve, respectively, an electromigration of the bioactive molecule M adjacent the target tissue T and an electroporation of a cell membrane within the target tissue T sufficient to permit entry of the bioactive molecule M into the cell interior.

A third method (FIG. 9) is for bringing two molecules M,M' into apposition at a desired target tissue site S for permitting a reaction therebetween, as in multicomponent labile system, or a cell "bomb." This method comprises the steps of introducing a substance containing a first molecule M into a first area A adjacent the target tissue site S and introducing a substance containing a second molecule M' into a second area A' adjacent the target tissue site S.

Next an electromigration of the first M and the second molecule M' is caused to a third area A' that is in the target tissue site S. The electromigration is caused by at least a pair of electrodes placed against a surface generally adjacent but in nonpenetrating fashion to a target tissue. The third area A" may actually comprise the first A or the second area A', or another area distinct therefrom.

Next the first M and the second M' molecule are permitted to react at the third area A".

It may be appreciated by one skilled in the art that additional embodiments may be contemplated, including alternate embodiments of the manipulator. In this application, a device being "configured" to produce an electromagnetic field in vivo means that (i) the portion of the device that comes in contact with body tissue or fluid is made of biocompatible materials, (ii) the electrodes are capable of carrying the current required for electroporation and/or electromigration of living cells in vivo in an electrolyte which may include the tissue being treated, interstitial fluid, injected material at the treatment site, material applied to the target tissue, and combinations of the foregoing, and (iii) the material between the electrodes on each support member, which may be the same material as the support member, should have a sufficient dielectric constant so that it does not break down as a result of nearby electrodes being of opposite polarity during electrical treatment. Additionally, a device being configured to be located against a selected portion of target tissue means that the shape, flexibility and material forming the device are such that the device can be located directly against the tissue. Moreover, it will be apparent to those skilled in the art that where an electrode or system is configured to perform both electromigration and electroporation, such an electrode or system may be used to perform either or both functions.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A device for manipulating a molecule in vivo relative to a target tissue comprising:

a support comprising a generally cylindrical post having a portal therethrough from a top end to a bottom end and at least two discrete electrodes extending away from and affixed to the support in spaced-apart relation from each other, each electrode being in circuit communication with a respective portion of a source of electrical energy;

a disc affixed to the post bottom end, the disc having a bottom surface having an outer downwardly depending annulus comprising alternating sectors of conductive and nonconductive areas, the electrodes comprising the conductive sectors; and leads in circuit communication with the conductive areas and extending from the disc through the post portal to the top end thereof;

the electrodes being configured to establish a first electromagnetic field between selected electrodes sufficient to manipulate a molecule relative to a target tissue and a second electromagnetic field sufficient to cause transient permeability of a cell membrane within the target tissue;

the device being configured so that at least two of the electrodes are locatable against a selected portion of the target tissue.

2. The device recited in claim 1, further comprising:

a plurality of contact means positioned adjacent the post portal top end and in circuit communication with each lead; and interface means positioned adjacent the post portal top end having means for communicating with each contact means for establishing circuit communication with a signal generator.

3. The device recited in claim 2, wherein:

each of the contact means comprises a contact brush affixed within the portal against an inner wall thereof; and the interface means comprises a key interlock insertable within the portal at the top end and having a contact pad positioned for communication with each contact brush.

4. The device recited in claim 1, wherein the disc comprises a flexible material to permit shape adaptation with the selected portion of the target tissue.

5. The device recited in claim 1, wherein the disc has a transparent portion to permit visualization of the target tissue selected portion therethrough.

6. The device recited in claim 1, further comprising means for delivering a preselected pattern of signals to selected pairs of electrodes to effect a desired molecular motion.

7. The device recited in claim 1, further comprising means for establishing at least one pair of opposite-polarity voltages approximately simultaneously on a respective pair of electrodes.

8. The device recited in claim 1, further comprising means for selectively activating each electrode in a predetermined pattern.

9. The device recited in claim 8, wherein the source of electrical energy comprises a signal generator and the activating means comprises software means in controlling relation to the signal generator.

10. The device recited in claim 1, wherein the support has a lumen therethrough adapted for admitting a syringe to permit an introduction of a substance containing the molecule into the target tissue.

11. A method for delivering a bioactive molecule front an initial location to a target tissue, the method comprising the steps of:

placing a plurality of pairs of electrodes against a surface generally adjacent but in nonpenetrating fashion to a target tissue, the pairs of electrodes disposed in generally opposed, alternating fashion on a annular member, each electrode being in circuit communication with a respective portion of a source of electrical energy;

activating a pair of electrodes to achieve an electromigration of the bioactive molecule from the initial location to a location adjacent the target tissue; and activating a pair of electrodes to achieve electroporation of a cell membrane within the target tissue sufficient to permit entry of the bioactive molecule into the cell interior.

12. A method for bringing two molecules from two respective initial locations into apposition at a desired target tissue site for permitting a reaction therebetween, the method comprising the steps of:

placing a plurality of pairs of electrodes against a surface adjacent a desired target tissue site, the surface comprising an annulus whereto the electrodes are affixed in a generally opposed, alternating configuration;

activating at least one pair of electrodes to cause an electromigration of the first and the second molecule to a third area adjacent the target tissue site; and permitting the first and the second molecule to react at the third area.

13. The method recited in claim 12, wherein the activating step comprises establishing an electrical potential between the pair of electrodes sufficient to cause the electromigration of the first and the second molecule in a desired direction.

14. A method for making a molecule electromanipulator comprising the steps of:

affixing a plurality of pairs of electrodes to a generally annular support in generally opposed, alternating, spaced-apart relation, each electrode differentially activatable;

providing circuit communication between each electrode and a source of electrical energy, the electrodes configured to establish a low-level electromagnetic field in vivo between selected electrodes for manipulating a molecule relative to a target tissue and a higher-level electromagnetic field for causing transient permeability of a cell membrane within the target tissue; and providing switching means between each electrode and the electrical energy source to permit differential activation of each electrode.

15. The method recited in claim 14, further comprising means for controlling the switching means adapted to activate the electrodes in a preselected pattern.

* * * * *